Figure 1:
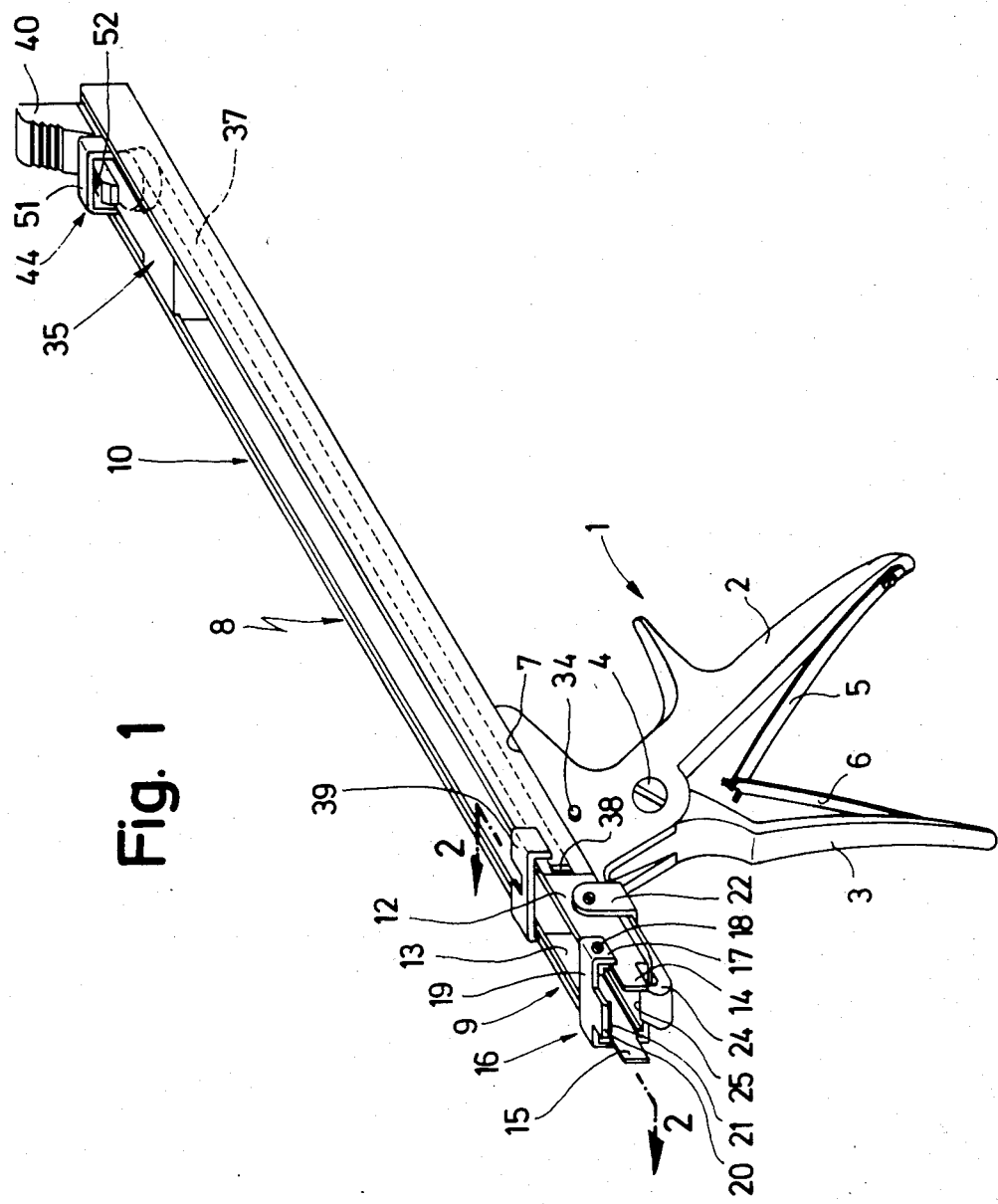

United States Patent [19]
Caspar et al.

[11] Patent Number: 4,637,395
[45] Date of Patent: Jan. 20, 1987

[54] APPLICATOR FOR C-SHAPED SCALP CLIPS

[75] Inventors: Wolfhard Caspar, Bad Homburg; Theodor Lutze, Balgheim; Karl-Ernst Kienzle, Immendingen, all of Fed. Rep. of Germany

[73] Assignee: Aesculap-Werke AG, Tuttlingen, Fed. Rep. of Germany

[21] Appl. No.: 657,269

[22] Filed: Oct. 2, 1984

[30] Foreign Application Priority Data

Oct. 4, 1983 [DE] Fed. Rep. of Germany ....... 3335986
Feb. 15, 1984 [DE] Fed. Rep. of Germany ....... 3405335

[51] Int. Cl.$^4$ ..................... A61B 17/00; A61B 17/04; A61B 17/12
[52] U.S. Cl. ............................. 128/334 R; 128/325; 128/346; 227/DIG. 1; 29/243.56
[58] Field of Search .................. 128/334 R, 325, 346; 24/260, 261; 29/243.56, 225; 227/DIG. 1

[56] References Cited

U.S. PATENT DOCUMENTS

| | | | |
|---|---|---|---|
| 3,075,199 | 11/1960 | Rose et al. | 72/410 |
| 3,307,389 | 3/1967 | Rose et al. | 128/334 R |
| 3,518,993 | 5/1967 | Blake | 227/DIG. 1 |
| 3,604,425 | 9/1971 | Le Roy | 128/325 |
| 3,955,581 | 5/1976 | Spasiano et al. | 128/334 R |
| 3,958,576 | 5/1976 | Komiya | 227/DIG. 1 |
| 4,246,903 | 1/1981 | Larkin | 128/325 |
| 4,372,316 | 2/1983 | Blake, III et al. | 128/325 |
| 4,396,139 | 8/1983 | Hall et al. | 227/19 |

Primary Examiner—Richard C. Pinkham
Assistant Examiner—Gary Jackson
Attorney, Agent, or Firm—Kenway & Jenney

[57] ABSTRACT

An applicator for C-shaped scalp clips, with which a plurality of scalp clips can be applied one after the other without having to insert an individual scalp clip into the applicator after each application. For this purpose, a magazine for receiving a plurality of scalp clips is provided and the scalp clips are arranged one behind the other in the magazine, the free ends of one scalp clip thereby resting against the bridge of the adjacent scalp clip, the magazine being open at the end to which the free ends of the legs of the scalp clips point, the scalp clips being guided in the magazine for displacement in the longitudinal direction thereof and moved towards the open end of the magazine by spring means, and the applying instruments, in a first position in which they are remote from one another, projecting downwardly and upwardly into the feed path of the scalp clips at the open end of the magazine such that a scalp clip which has been moved past the applying instruments abuts thereon with its laterally projecting edge regions adjoining the application surfaces and, in a second position in which the applying instruments are brought closer together, these instruments abutting on the application surfaces of the scalp clip held between them and thereby opening the scalp clip.

18 Claims, 9 Drawing Figures

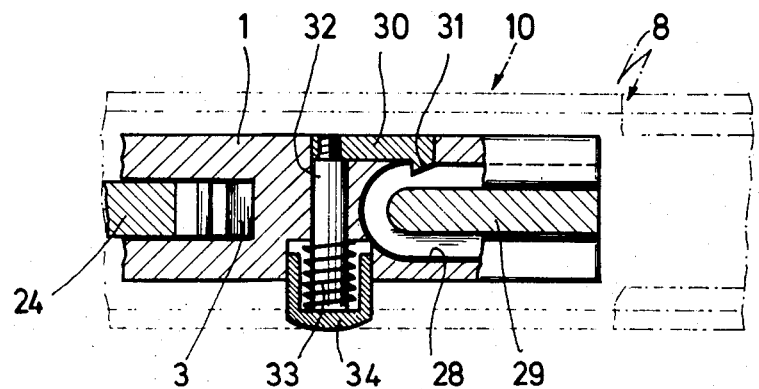
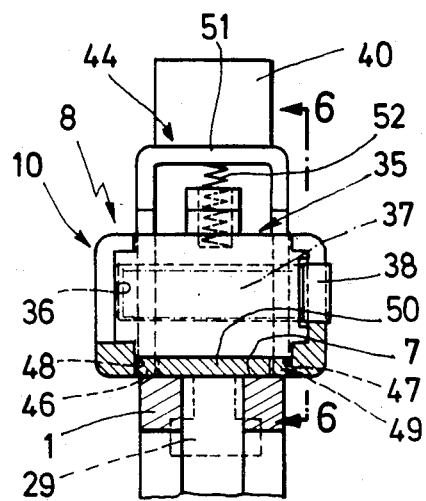
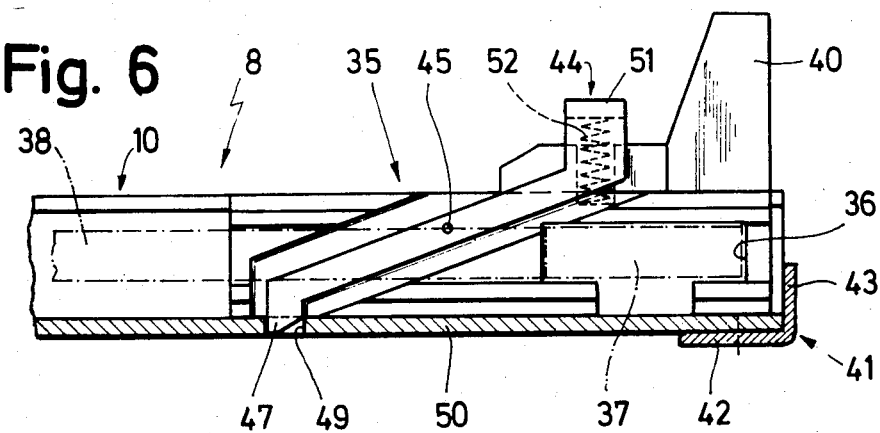

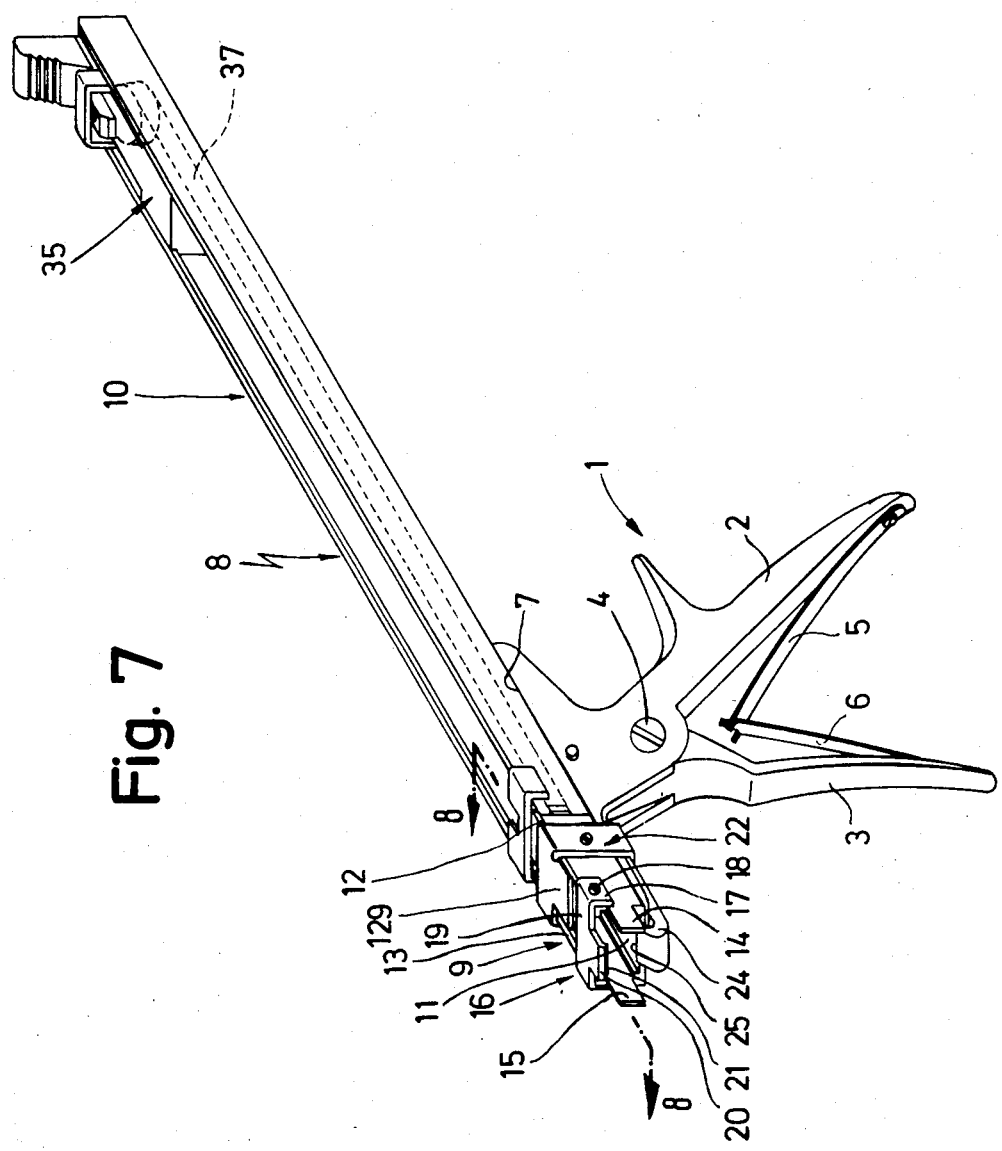

APPLICATOR FOR C-SHAPED SCALP CLIPS

The invention relates to an applicator for C-shaped scalp clips which have two legs joined by a bridge and facing clamping jaws at their free ends as well as rearwardly projecting application surfaces at the regions where the legs and bridge meet and laterally projecting edge regions adjoining the application surfaces, the applicator comprising two applying instruments adapted to be applied to the application surfaces of a scalp clip and displaced towards one another for opening this scalp clip. Scalp clips of this type and their applicators are known, for example, from U.S. Pat. No. 3,604,425. A quite normal, forceps-like device is used for bending open the scalp clips described in this patent. The two branch elements of this device rest against rearwardly extending projections of the scalp clip and enable the scalp clip to be opened when they are closed. However, only single scalp clips can be applied with this device and each scalp clip has to be inserted separately into the applicator.

The object of the invention is to improve an applicator for scalp clips of this type such that a plurality of scalp clips can be applied one after the other without any complicated insertion of the scalp clips into the applicator being necessary each time.

This object is accomplished, according to the invention, for an applicator of the type described at the outset in that a magazine for receiving a plurality of scalp clips is provided and the scalp clips are arranged one behind the other in the magazine, the free ends of one scalp clip thereby resting against the bridge of the adjacent scalp clip, that the magazine is open at the end to which the free ends of the legs of the scalp clips point, that the scalp clips are guided in the magazine for displacement in the longitudinal direction thereof and moved towards the open end of the magazine by spring means, and that the applying instruments, in a first position in which they are remote from one another, project downwardly and upwardly into the feed path of the scalp clips at the open end of the magazine such that a scalp clip which has been moved past the applying instruments abuts thereon with its laterally projecting edge regions adjoining the application surfaces and, in a second position in which the applying instruments are brought closer together, the instruments abut on the application surfaces of the scalp clip held between them and thereby open the scalp clip.

The use of such a magazine enables a larger number of scalp clips to be kept ready for use and applied one after the other with the same applicator without a new scalp clip having to be inserted into the device after each application. The scalp clips which are stored one behind the other in the magazine are pushed towards the applying instruments one after the other under the influence of the spring means. At the same time, the applying instruments brake the forward movement of the leading scalp clip as soon as this clip reaches its applying position and, when moved accordingly, bend the scalp clip open so that it can be applied to a wound. Once applied, the scalp clip is open further than in its basic state due to the tissue clamped between the clamping jaws. This means that the laterally projecting edge regions are closer together. This enables the applicator to be removed from the scalp clip once applied, i.e. the scalp clip can be extracted from between the applying instruments due to the smaller distance between its edge regions.

It is favourable to have the legs of the scalp clips, in their closed state, converging towards their free ends. This ensures that the scalp clips can enter between the applying instruments when they are moved forward until the laterally projecting edge regions come to rest on the applying instruments.

In a preferred embodiment, one of the applying instruments can be held stationary on the magazine. In this case, only the other applying instrument is moved for the purpose of opening the scalp clip.

One applying instrument is preferably mounted on the magazine for pivoting movement about an axis extending transversely to the longitudinal axis of the magazine and is adapted to be pivoted by actuating means from the first to the second position.

The actuating means can thereby comprise two branch elements, of which the first is rigidly secured to the magazine while the second is pivotable towards the first and the pivotable branch element can be in operative connection with the pivotable applying instrument.

A particularly advantageous embodiment is one with which the magazine is designed in two parts, whereby the front part including the open end of the magazine and the applying instruments is adapted to be detachably connected to a rear part accommodating a plurality of scalp clips. In this way, the magazine can be filled quite simply in that the rear part is detached from the front part and the scalp clips inserted therein. After it has been filled with scalp clips, the rear part is reconnected to the front part to form a complete applicator.

It can be advantageous for the two parts of the magazine to be rigidly connected in their positions by means of a detachable, flexible locking connection. In this way, the two parts can be detached from one another and reconnected in the simplest possible manner.

In order to effectively open the scalp clips, the applying instruments can have edges extending transversely to the longitudinal axis of the magazine and abutting on the application surfaces of the scalp clips.

In a preferred embodiment of the invention, a slider is mounted for displacement in the magazine, this slider resting resiliently against the scalp clips in the magazine under the influence of the spring means and pushing the scalp clips towards the open end. It is thereby favourable for the slider to be adapted to be secured in its retracted position so that the magazine can then be filled from the front.

A particularly favourable development is one with which the spring means is a coil spring which is located in the interior of the slider and the free end of which is secured to the magazine near the open end thereof. This coil spring has the tendency to wind itself into its spiral form and so it exerts pressure on the slider to push it towards the point of attachment of the spring.

Preferably, the coil spring is designed as a leaf spring and abuts on one wall of the magazine adjacent the scalp clips. This means that the space required by the leaf spring in the cross section of the magazine is minimal.

With the embodiments described so far, it may happen that the leading clip will be pushed past the applying instruments due to the spring force exerted on it and fall out of the magazine when the applying instrument is unfavourably positioned.

It is therefore a further object of the invention to develop a scalp clip applicator of this type further to ensure that no scalp clip is inadvertently pushed out of the magazine.

This object is accomplished, according to the invention, for a scalp clip applicator of the type described at the outset in that a retaining element is provided which dips into and is displaceable out of the feed path of the scalp clips, is disposed before the applying instruments by approximately the length of a scalp clip and retains that clip which follows directly behind the scalp slip gripped by the applying instruments.

This ensures that the next scalp clip following that gripped by the applying instruments cannot be pushed forward into the region of application until the retaining element is displaced out of its feed path.

It is particularly advantageous for the retaining element to be displaceable simultaneously with the applying instruments such that it is withdrawn from the feed path when the applying instruments are in their second position (applying position) whereas it dips into the feed path when the applying instruments are in their first position (inoperative position).

Therefore, any further forward movement of the clips is automatically prevented when the applying instruments are in their inoperative position, i.e. when there is the greatest risk of the scalp clips being pushed past these applying instruments in an undesired manner. When, on the other hand, the applying instruments are in their applying position, a scalp clip cannot inadvertently exit from the magazine, i.e. in this position of the applying instruments the retaining element of the advantageous development is withdrawn from the feed path. Nevertheless, it is not possible for the next scalp clip to be pushed forward into the region of application since any further forward movement is prevented by the scalp clip gripped between the applying instruments. In order to move the next following scalp clip forward into the region of application, the applying instruments must be moved briefly into their second position (applying position), once the scalp clip just applied has been released, so that the retaining element is withdrawn for a short time from the feed path. The scalp clip retained by the retaining element up to that time can then slide past this retaining element but will be prevented from exiting from the magazine by the applying instruments which have been moved into their applying position, i.e. it is ensured that the applying instruments will now safely grip the new leading scalp clip.

It is particularly advantageous when the retaining element is rigidly connected to a movable applying instrument.

In particular, the movable applying instrument and the retaining element rigidly connected thereto can be provided on opposite sides of the magazine.

In a preferred embodiment, the retaining element is pivotable about an axis extending transversely to the feed path of the scalp clips in the magazine.

It is also advantageous for the retaining element to have a retaining nose which rests against one of the laterally projecting application surfaces of the scalp clip when the retaining element dips into the clip feed path.

The following description of preferred embodiments serves to explain the invention in more detail in conjunction with the drawings.

Figure 2:
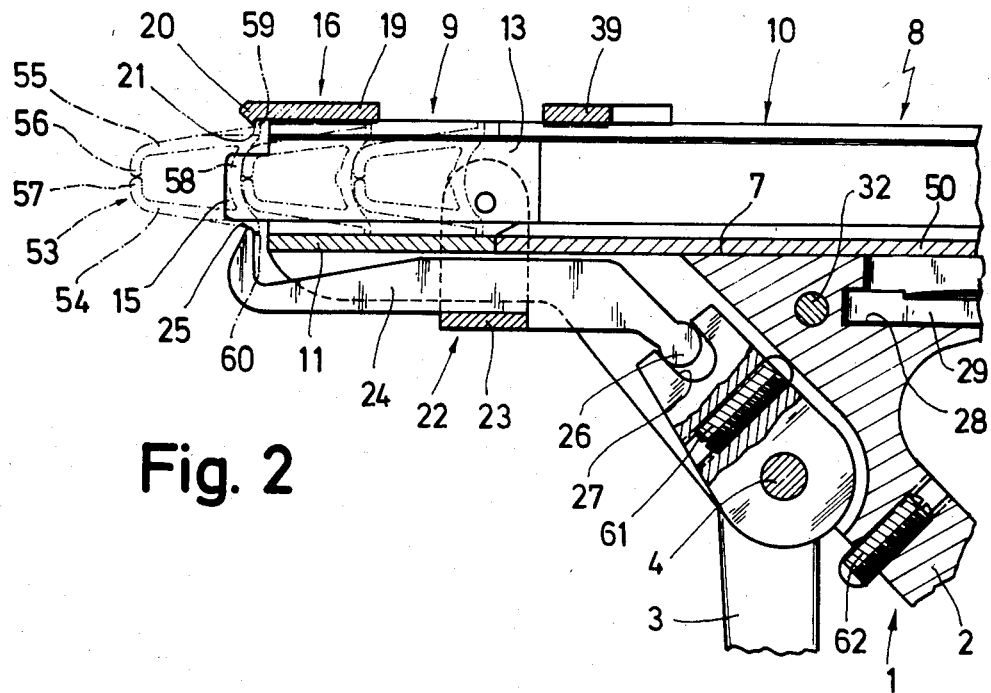
Figure 3:
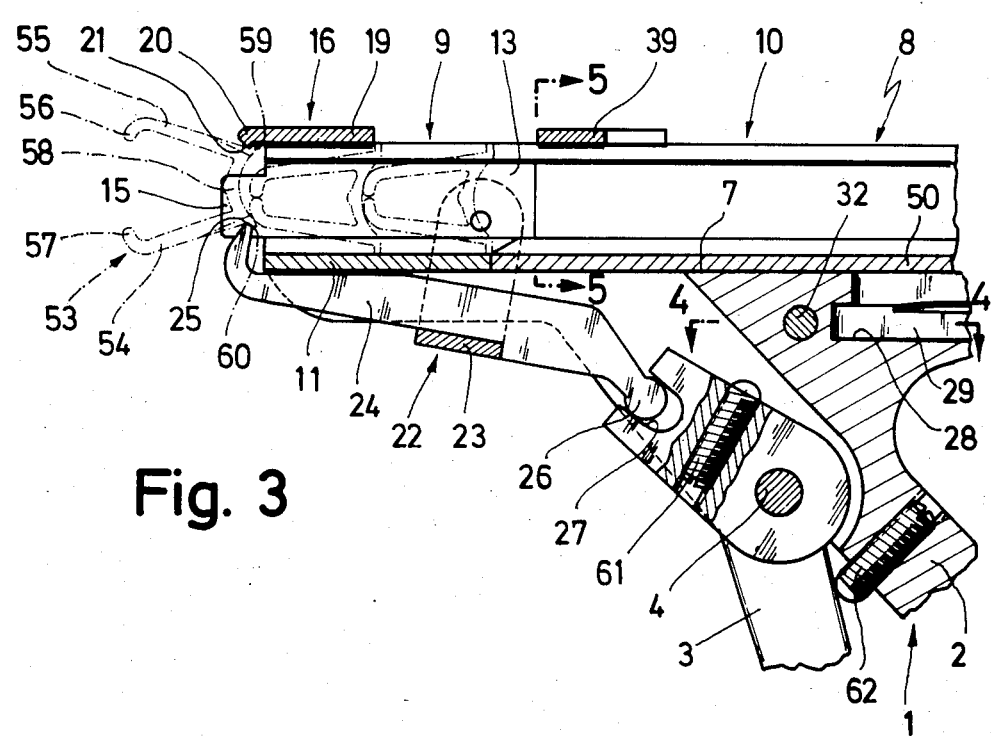
Figure 8:
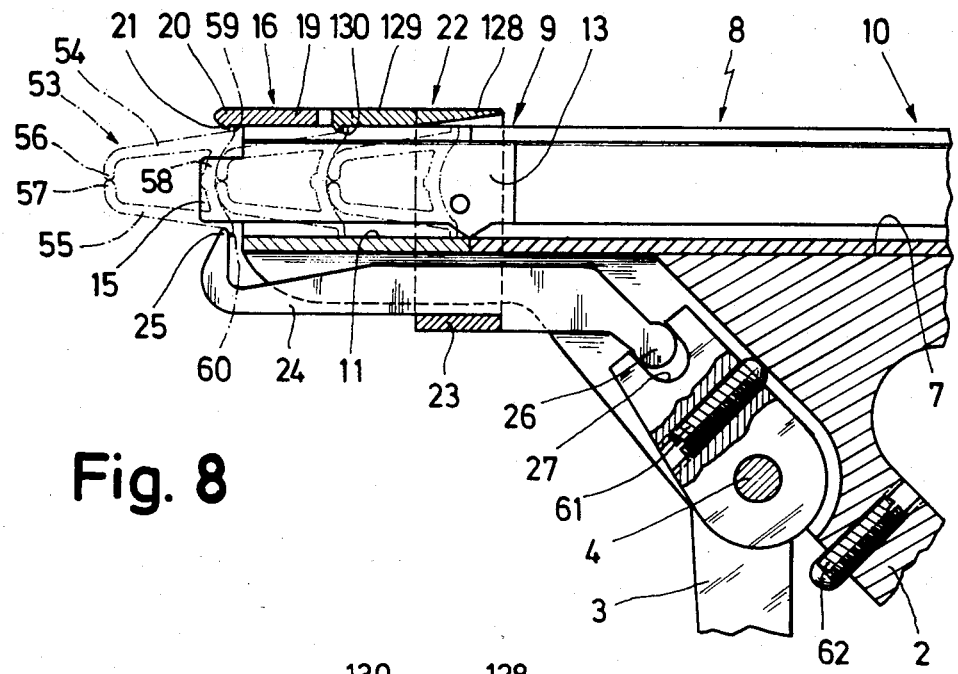
Figure 9:
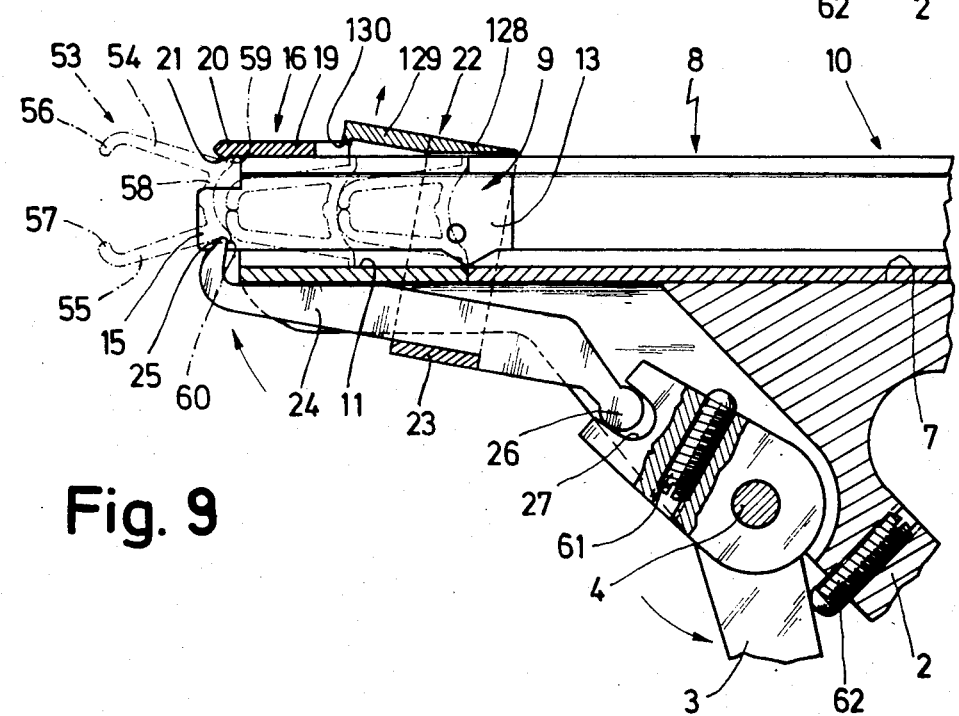

FIG. 1 is a perspective view of an applicator;
FIG. 2 is a sectional view along line 2—2 in FIG. 1;
FIG. 3 is a view similar to FIG. 2 with one applying instrument pivoted inwards;
FIG. 4 is a sectional view along line 4—4 in FIG. 3;
FIG. 5 is a sectional view along line 5—5 in FIG. 3;
FIG. 6 is a sectional view along line 6—6 in FIG. 5;
FIG. 7 is a perspective view of a further, preferred embodiment of an applicator;
FIG. 8 is a sectional view along line 8—8 in FIG. 7 and
FIG. 9 is a view similar to FIG. 8 with one applying instrument pivoted inwards and the retaining element displaced outwards.

The applicator illustrated in the drawings comprises a holder 1, which has a stationary handle or branch element 2. A second branch element 3 is pivotally connected to this branch element 2 and a screw 4 which penetrates both branch elements is provided for mounting the second branch element 3 on the first branch element 2. Two leaf springs 5 and 6 are disposed between the free ends of the two branch elements 2 and 3. These springs are attached at one end to the branch elements and rest against each other at their other ends so that the two branch elements 2 and 3 are pivoted flexibly apart by these two springs (FIG. 1).

The holder 1 has on its upper side an application surface 7, onto which the magazine 8 is placed. This magazine has a front part 9 and an elongated rear part 10. The front part has a U-shaped cross section, rests with its base 11 on the application surface 7 of the holder 1 and is rigidly connected to the holder 1 by, for example, two screws which are not illustrated in the drawing. The front part 9 is open at its free end; in this region the two side walls 12 and 13 bear projecting lips 14 and 15. Their function will be explained later on. A U-shaped bridge 16 is arranged above the open free end of the front part 9. The arms 17 of this bridge rest against the outside of the side walls 12, 13 of the front part 9 and are fixed in position by screws 18. The two arms 17 of the bridge 16 are connected by a crosspiece 19 which bears at its front end a downwardly bent tongue 20, the free edge 21 of which dips slightly into the cross section of the magazine 8.

At the rear end of the front part 9, a U-shaped bracket 22 is mounted on the two side walls 12 and 13 for pivoting movement about a horizontal axis. The crosspiece 23 of this bracket passes beneath the holder 1. A lower applying instrument 24 is secured to this crosspiece 23 and is disposed in a longitudinal central groove of the holder 1 which is open to the front. At its free end, it has an upwardly projecting edge 25, which is opposite the edge 21 and protrudes from below into the cross section of the magazine 8. The applying instrument 24 is provided at its end opposite the edge with a bead 26 which is circular in cross section and engages in an open longitudinal groove 27 in the second branch element 3 mounted on the first for pivoting movement (FIGS. 2 and 3). When the branch element 3 is pivoted, the applying instrument is moved with it and pivoted about the axis of rotation defined by the attachment of the lateral arms of bracket 22 on the side walls 12 and 13 of the front part 9. This pivoting movement brings the edge 25 closer to the edge 21 of the bridge 16, i.e. the edge 25 dips further into the open cross section of the magazine 8.

The considerably longer rear part 10 of the magazine 8 has the same cross section as the front part 9. The rear part 10 may be secured to the holder 1 such that front part 9 and rear part 10 are directly adjacent to one another. The rear part may also converge towards its free end while the front part is of a complementary design on the side facing the rear part. In this way, the rear part is automatically centered when brought up to the front part. The holder 1 is provided with a longitudinal groove 28 which is open towards the rear and has a T-shaped cross section, into which a T-shaped guide element provided on the underside of the rear part 10 may be inserted so as to lie closely against the surfaces of the longitudinal groove 28. In order to connect the front part and rear part with one another, the holder has a lateral detent 30 which, when inserted, engages in a lateral recess in the T-shaped guide element 29 (FIG. 4). The detent 30 is held on a pin 32 which penetrates the holder 1 and is encircled by a coil spring 33. This spring is supported on one side on a press stud 34 of the pin 32 and on the other side on the holder 1 and draws the pin and the detent 30 into the recess 31. By pressing the press stud 34, the pin and detent may be displaced contrary to the action of the spring 33 such that the detent 30 exits from the recess 31 and allows the rear part 10 to be removed from the holder 1.

A slider 35 is mounted for displacement in the rear part 10 and substantially fills the entire cross section of this rear part. A spirally wound leaf spring 37 is arranged in the hollow interior 36 of the slider. The free end 38 of this leaf spring exits laterally from the interior 36 and extends as far as the front end of the rear part, thereby resting closely against the inside of the side wall of the rear part 10. At the front end of this rear part, the free end 38 is secured to the inside of the side wall of the rear part. Since the leaf spring 37 has the tendency to wind itself helically, the free end exerts a spring force on the slider 35 to push the slider towards the front end of the rear part 10. During this forward movement the leaf spring winds itself in the interior of the slider 35. In order to prevent the slider exiting from the rear part, a bridge 39 is arranged at the front end of the rear part 10, across the upper open side, and forms a stop for the slider.

The slider itself has on its rear side an upwardly projecting grip portion 40, with which the slider may be displaced into its rearward position. At its rear end, the rear part 10 is open, except for an L-shaped stop 41, one leg 42 of which is secured to the bottom of the rear part 10 while the other leg 43 projects upwardly into the opening and thereby prevents the slider being pushed too far out.

In order to be able to secure the slider in its rearward position, a U-shaped bracket 44 is mounted on the slider for pivoting movement about a horizontal axis 45. The two free ends 46 and 47 thereof dip into two bores 48 and 49 in the bottom 50 of the rear part 10 through recesses in the side walls (FIG. 6). When a force is exerted on the crosspiece 51 connecting the two ends, the bracket can be pivoted such that the two ends 46 and 47 exit from the bores 48 and 49 and so the slider can be freely displaced. Due to a pressure spring 2 between the crosspiece 51 and the slider 35, the bracket 44 is biased such that the free ends 46 and 47 are pressed against the bottom 50 or into the bores 48 and 49.

The applicator described is intended to receive scalp clips 53 which are illustrated in the drawings by dash-dot lines. These scalp clips essentially have a C-shaped cross section with a pair of legs 54 and 55 converging towards their free ends. These legs have clamping jaws 56 and 57 at their free ends and are connected with one another at their opposite ends by a bridge 58 which is concave in design. The scalp clips are preferably produced in one piece from plastic and are closed in their normal state, i.e. the two clamping jaws 56 and 57 rest against one another.

In operation, a large number of scalp clips 53 are first inserted into the rear part 10 of the magazine, from the front, when the slider is retracted and held in this position. The clips are thereby inserted such that their concave bridges face the slider. After insertion, the free ends of one clip fit against the concave bridge of the clip in front, as shown, for example, in FIG. 2.

As soon as the rear part 10 is filled with clips it is pushed into the holder 1 and held in place by the detent 30. The slider is then released by pressure being exerted on the crosspiece 51 and the slider pushes the scalp clips into the front part 9 until the leading scalp clip is prevented from moving further forward by the edge 21 of the bridge 16 and by the edge 25 of the lower applying instrument 24. For this purpose, the scalp clips have laterally projecting edges 59 and 60 in the regions where the bridge 58 and the legs 54 and 55 meet. These edges abut on the edge 21 or edge 25 (leading clip in FIG. 2). The position of the lower applying instrument 24 which is required for this can be adjusted by a setscrew 61 which penetrates the second branch element 3 and abuts on the first branch element 2 with its free end (FIG. 2).

As shown in the illustration of FIG. 2, the leading scalp clip, in its basic position, protrudes beyond the front end of the magazine 8 and is laterally guided by the laterally projecting lips 14 and 15 on the front part 9 of the magazine 8.

For the purpose of applying the scalp clip, the branch element 3 is pivoted towards the branch element 2 contrary to the action of leaf springs 5 and 6 and simultaneously pivots the lower applying instrument 24 such that the edge 25 is brought closer to the edge 21. In this way, the scalp clip is bent such that its rear edges are closer together and it opens at the front in the way shown in FIG. 3 due to the concave design of the bridge 58. The extent to which the clip is bent open may be adjusted by a setscrew 62 which penetrates the first branch element 2 and, by resting against the second branch element 3, limits the pivoting movement of this second branch element.

In the operative position illustrated in FIG. 3, the scalp clip can now be applied, i.e. it is moved over a layer of tissue such that the tissue is positioned between its pair of clamping jaws. If branch element 3 is then released it is withdrawn from branch element 2 under the force of the leaf springs 5 and 6 so that the edge 25 is also withdrawn again from edge 21. The scalp clip thereby closes, although no longer completely due to the tissue now located between the clamping jaws. For this reason, the distance between the two edges 59 and 60 is smaller than for a scalp clip which is not bent open. It is then possible for the applying instrument to be withdrawn from the scalp clip since the smaller distance between edges 59 and 60 means that these can pass between the edge 25 and the edge 21 when the lower applying instrument 24 is again in its inoperative position.

All the scalp clips in the magazine 8 are now moved forward under the influence of the slider, which is pushed forward by spring force, until the next following scalp clip, which is now the leading clip, reaches the position of application illustrated in FIG. 2.

This procedure may be repeated until the magazine is empty. In order to refill the magazine it is sufficient to release the detent 30 by pressing on the press stud 34 and withdrawing the rear part 10 from holder 1. The rear part can then be refilled with scalp clips from the front and reattached to the holder 1.

It is, of course, also possible to combine a plurality of rear parts 10 with an applicator so that a rear part 10 filled with clips can be pushed onto the applicator as soon as a first rear part is empty.

In the embodiment illustrated in FIGS. 7 to 9, which is constructed in a very similar manner, the same reference numerals are used to designate the same parts.

A forwardly extending projection 129 is arranged on a crosspiece 128 of the bracket 22, this crosspiece being arranged above the magazine. The projection has a downwardly extending retaining nose 130 at its free end. In the inoperative position (vide FIG. 8) of the lower applying instrument rigidly connected to the holder, the retaining nose projects into the feed path of the scalp clips which are moved forward in the magazine. In the applying position of the applying instrument, the retaining nose 130 is pivoted out of the feed path.

The retaining nose 130 is set back in relation to the edge 21 of the upper applying instrument by the length of a scalp clip, as shown in the illustration of FIG. 8.

As also shown in FIG. 8, the leading scalp clip, in its basic position, projects beyond the front end of the magazine 8 and is laterally guided by the laterally projecting lips 14 and 15 on the front part 9 of the magazine 8.

At the same time, in this basic position, the retaining nose 130 of the projection 129 abuts on the upper edge 59 of the second clip and thus prevents this second clip and the following clips from being pushed against the leading clip, which is in the applying position (FIG. 8), by the spring-loaded slider 35.

When the applying instrument moves into its applying position (FIG. 9), the retaining nose 130 is pivoted out of the feed path of the scalp clips so that the second clip is released. This clip cannot, however, move further forward in the magazine as it is prevented from doing so by the leading clip bent open by the applying instruments.

When the applying instrument 25 is again pivoted out of the applying position, the retaining element with the retaining nose 130 simultaneously enters the feed path again and holds the scalp clip, which is now the leading clip, securely in a position set back relative to the actual position of application.

In order to move the leading scalp clip into an applying position it is sufficient to bring the branch elements momentarily closer together so that the retaining nose 130 exits from the feed path. The leading scalp clip is thereby released and moved forward by the slider 35. The clip cannot exit completely from the magazine as the applying instrument 24 is also pvioted towards the applying position due to the release of the retaining element and therefore prevents the leading clip from exiting completely. The clip can be moved forward only until its edges 59 and 60 rest against the edge 21 and the edge 25. The leading clip is held securely in this applying position. If the branch elements are released, the retaining nose 130 moves in front of the upper edge 59 of the next following scalp clip and thereby holds this following clip back, i.e. the leading clip is no longer pushed out of the magazine by the spring force of the leaf spring 37. Even if the scalp clip could be pushed out of the magazine by a strong thrusting force, when the applying instrument 24 is pivoted out of its applying position, there is no danger of this happening unintentionally as the leading scalp clip is not subject to the action of the leaf spring 37 in this position. Any force exerted by the leaf spring 37 after the leading clip has been bent open is not detrimental since, in this phase of operation, the applying instrument 24 is pivoted in and holds the leading clip firmly and securely in the magazine.

This procedure may be repeated until the magazine is empty. Due to provision of a retaining element which can be pivoted in and out it is possible to move the clips forward with a considerable spring force without any danger arising of a scalp clip being pushed unintentionally out of the magazine. It is also advantageous for the next scalp clip to be applied to be able to remain completely within the interior of the magazine until it is intended to be applied. This considerably reduces the risk of the scalp clip becoming soiled. Not until the scalp clip is intended to be applied is it released by a brief movement of the branch elements and pushed forward into the applying position. Only then will it be bent open and applied. Once this clip has been applied, the following clips are again located completely in the interior of the magazine.

What is claimed is:

1. An applicator for C-shaped scalp clips which have two legs joined by a bridge and facing clamping jaws at their free ends, rearwardly projecting application surfaces at the regions where the legs and bridge meet, and laterally projecting edge regions adjoining the application surfaces, comprising two applying instruments movable between first and second positions and positioned to engage the application surfaces of a scalp clip and displace them towards one another for opening said scalp clip when said applying instruments are in said second position, a magazine that holds a plurality of the scalp clips arranged one behind the other, with the free ends of one scalp clip resting against the bridge of the adjacent scalp clip, said magazine being open at the end to which the free ends of the legs of the scalp clips point, and guiding the scalp clips for displacement in the longitudinal direction thereof, and means for urging the scalp clips towards the open end of the magazine, said applying instruments in the first position being remote from one another, projecting downwardly and upwardly into the feed path of the scalp clips at said open end such that one of said scalp clips moved by said urging means past said applying instruments abuts thereon with said laterally projecting edge regions adjoining the application surfaces and in the second position being closer together with said instruments abutting on the application surfaces of one of said scalp clips held between them and thereby opening said one scalp clip.

2. Applicator as defined in claim 1, wherein the legs (54, 56) of the scalp clips (53), in their closed state, converge towards their free ends.

3. Applicator as defined in claim 1, wherein one applying instrument (edge 21) is held stationary on the magazine (8).

4. Applicator as defined in claim 1, wherein one applying instrument (edge 25) is mounted on the magazine (8) for pivoting movement about an axis extending transversely to the longitudinal axis of the magazine and is adapted to be pivoted from the first to the second position by actuating means (branch elements 2 and 3).

5. Applicator as defined in claim 4, wherein the actuating means comprises two branch elements (2, 3), of which the first is rigidly secured to the magazine (8) while the second is pivotable towards the first, the pivotable branch element (3) being in operative connection with the pivotable applying instrument (24, 25).

6. Applicator as defined in claim 1, wherein the magazine (8) is designed in two parts, whereby the front part (9) including the open end of the magazine (8) and the applying instruments (edge 21, edge 25) is adapted to be detachably connected to a rear part (10) accommodating a plurality of scalp clips (53).

7. Applicator as defined in claim 6, wherein the two parts (9, 10) of the magazine are rigidly connected in their positions by means of a detachable flexible locking connection (30, 31).

8. Applicator as defined in claim 1, wherein the applying instruments have edges (21, 25) extending transversely to the longitudinal axis of the magazine and abutting on the application surfaces of the scalp clips (53).

9. Applicator as defined in claim 1, wherein a slider (35) is mounted for displacement in the magazine (8), the slider resting resiliently against the scalp clips (53) in the magazine (8) under the influence of the urging means (37) and pushing the scalp clips towards the open end.

10. Applicator as defined in claim 9, wherein the slider (35) is adapted to be secured in its retracted position.

11. Applicator as defined in claim 9, wherein the urging means is a spiral spring (37) located in the interior of the slider (35), the free end (38) of the coil spring being secured to the magazine (8) near the open end thereof.

12. Applicator as defined in claim 11, wherein the spiral spring is designed as a leaf spring (37) abutting on one wall of the magazine (8) adjacent the scalp clips (53).

13. Applicator for C-shaped clips which have two legs joined by a bridge and facing clamping jaws at their free ends, rearwardly projecting application surfaces at the regions where the legs and bridge meet, and laterally projecting edge regions adjoining the application surfaces, comprising
two applying instruments movable between first and second positions positioned to engage the application surfaces of a scalp clip and displace them towards one another for opening said scalp clip,
a magazine that holds a plurality of scalp clips arranged one behind the other in the magazine with the free ends of one scalp clip resting against the bridge of the adjacent scalp clip, said magazine being open at the end to which the free ends of the legs of the scalp clips point, and guiding the scalp clips in the magazine for displacement in the longitudinal direction thereof,
spring means for moving the scalp clips towards the open end of the magazine,
said applying instruments, in the first position being remote from one another, projecting downwardly and upwardly into the feed path of the scalp clips at said open end such that one of said scalp clips moved by said urging means past said applying instruments abuts thereon with said laterally projecting edge regions adjoining the application surfaces and in the second position being closer together with said instruments abutting on the application surfaces of one of said scalp clips held between them and thereby opening said one scalp clip, and,
a retaining element dipping into and being displaceable out of the feed path of the scalp clips, said retaining element also being disposed before the applying instruments by approximately the length of a scalp clip and retaining that clip which follows directly behind the scalp clip gripped by the applying instruments.

14. Applicator as defined in claim 13, wherein the retaining element (129, 130) is adapted to be displaceable simultaneously with the applying instruments such that it is withdrawn from the feed path when the applying instruments are in their second position (applying position) whereas it dips into the feed path when the applying instruments are in their first position (inoperative position).

15. Applicator as defined in claim 14, wherein the retaining element (129, 130) is rigidly connected to a movable applying instrument (24).

16. Applicator as defined in claim 15, wherein the movable applying instrument (24) and the retaining element (129, 130) rigidly connected thereto are arranged on opposite sides of the magazine (8).

17. Applicator as defined in claim 13, wherein the retaining element (129, 130) is pivotable about an axis extending transversely to the feed path of the scalp clips (53) in the magazine (8).

18. Applicator as defined in claim 13, wherein the retaining element has a retaining nose (130) resting against one of the laterally projecting application surfaces (edge 59) of the scalp clip (53) when the retaining element dips into the clip feed path.

* * * * *